United States Patent [19]

Adams et al.

[11] 4,032,554

[45] June 28, 1977

[54] COUPLING AGENT FOR FIBROUS GLASS SUBSTRATES

[75] Inventors: Richard G. Adams, Montclair; Stephen B. Sello, Cedar Grove, both of N.J.

[73] Assignee: J. P. Stevens & Co., Inc., New York, N.Y.

[22] Filed: Feb. 2, 1976

[21] Appl. No.: 654,324

Related U.S. Application Data

[62] Division of Ser. No. 412,943, Nov. 5, 1973, abandoned.

[52] U.S. Cl. .................................. 260/448.8 R
[51] Int. Cl.² ...................... C07F 7/10; C07F 7/18
[58] Field of Search ........................ 260/448.8 R

[56] References Cited

UNITED STATES PATENTS 3,772,346  11/1973  Hess ........................ 260/448.8 R

*Primary Examiner*—Paul F. Shaver
*Attorney, Agent, or Firm*—Michael T. Frimer; Charles Stein

[57] ABSTRACT

This invention is directed to the use as coupling agents or bonding agents for fibrous glass substrates of compounds of the formula

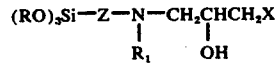

wherein R at each occurrence is independently an alkyl group of 1 to 5 carbon atoms,
X is chlorine or bromine,
$R_1$ is hydrogen, alkyl of 1 to 5 carbon atoms or

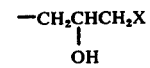

and
Z is selected from the group consisting of

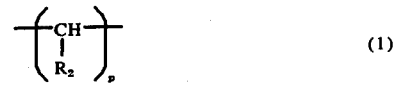

where
$R_2$ at each occurrence is independently hydrogen or alkyl of 1 to 5 carbon atoms and
p is an integer of 1 to 4, and

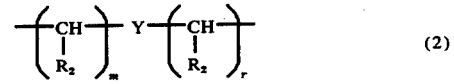

where
m and r are integers of 1 to 3,
$R_2$ has the meaning given above, and
Y is —S— or —O—

Laminates having excellent resistance to water exposure are obtained when glass substrates treated with the above coupling agents are impregnated with a thermosetting resin such as epoxy and polyester resins.

2 Claims, No Drawings

COUPLING AGENT FOR FIBROUS GLASS SUBSTRATES

This is a division of application Ser. No. 412,943, filed Nov. 5, 1973 now abandoned.

FIELD OF THE INVENTION

This invention relates to the use of certain silyl amine compounds containing chlorine or bromine atoms as coupling agents for fibrous glass substrates.

BACKGROUND OF THE INVENTION

Heretofore fibrous glass substrates such as glass fabric have been coated with compounds which serve as coupling agents or bonding agents between the glass and a thermosetting resin applied thereon. U.S. Pat. No. 3,682,975, issued Aug. 8, 1972, discloses the use as coupling agents of silyl epoxyalkylamines of the formula:

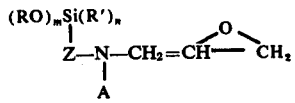

wherein
A is selected from the group consisting of hydrogen, alkyl, aryl, alkaryl and aralkyl;
m is an integer from 0 to 3;
n equals the quantity (3-m);
each R and R' is selected independently from the group consisting of alkyl, alkoxyalkyl, aryl, alkaryl, and aralkyl; and
Z is a divalent organic radical.

These compounds are prepared by reacting a substituted silyl amine with an epihalohydrin to form a substituted silyl-3-halo-2-hydroxyalkylamine and then subjecting this intermediate compound to dehydrohalogenation with ring closure to form the desired silyl epoxyalkylamine compound. While such epoxy compounds are good coupling agents for fibrous glass substrates, the dehydrohalogenation step is difficult and expensive.

SUMMARY OF THE INVENTION

In accordance with the present invention it has been discovered that certain of the silyl-3-halo-2-hydroxyalkylamine compounds disclosed by U.S. Pat. No. 3,682,975 as intermediates are excellent as coupling agents between fibrous glass substrates and thermosetting resins, thus avoiding the above-mentioned dehydrohalogenation step. The coupling agents used in the present invention are derived from primary or secondary amine starting materials and a particularly preferred group of compounds differ from the intermediates disclosed in the above patent in that they are derived from primary amines and both hydrogen atoms of the amine group are replaced.

DETAILED DESCRIPTION OF THE INVENTION

The coupling agents of this invention are compounds of the formula

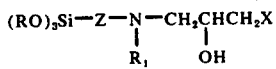

wherein
R at each occurrence is independently an alkyl group of 1 to 5 carbon atoms,
X is chlorine or bromine,
$R_1$ is hydrogen, alkyl of 1 to 5 carbon atoms or

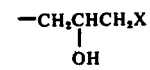

and
Z is selected from the group consisting of

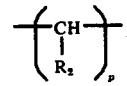 (1)

where
$R_2$ at each occurrence is independently hydrogen or alkyl of 1 to 5 carbon atoms, and
p is an integer of 1 to 4, and

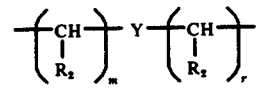 (2)

where
m and r are integers of 1 to 3,
$R_2$ has the meaning given above, and
Y is -S- or -O-
These compounds are prepared by reacting an amine of the formula:

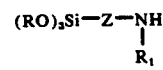

wherein
R, $R_1$ and Z have the meanings given above with epichlorohydrin or epibromohydrin.
The preferred coupling agents are compounds of the formula:

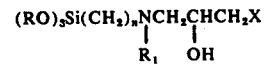

wherein
R, X and $R_1$ have the meanings given above, and
n is an integer of 1 to 4.
These compounds are prepared by reacting an amine of the formula

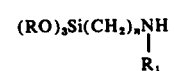

wherein
R, $R_1$ and n have the meanings given above with epichlorohydrin or epibromohydrin.
A particularly preferred group of compounds is obtained by using a primary amine and at least 2 moles of epichlorohydrin or epibromohydrin per mole of the amine to replace both hydrogens of the amine group. This reaction is illustrated by the following equation:

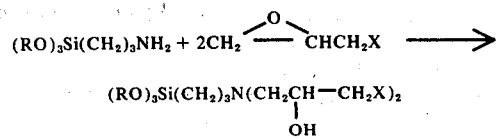

$$(RO)_3Si(CH_2)_3N(CH_2\underset{OH}{CH}-CH_2X)_2 \quad I$$

wherein R, n and X have the meanings given above. These coupling agents are novel compounds.

The reaction of the amine with the epihalohydrin is exothermic and should be maintained at a temperature of not more than about 85° C., preferably in the range of 0° to 80° C., in order to prevent formation of a gelled product. The reaction mixture can be moderately diluted by means of an inert organic solvent such as benzene, toluene, xylene, methyl cellosolve or methanol. Also, the product obtained can be moderately diluted by the addition of one of these inert solvents.

Preferably, the coupling agent, along with any inert organic solvent utilized is dissolved in water to form a dilute solution, e.g., one percent by weight of coupling agent, and this solution is applied to the fibrous glass substrate by a padding operation. Other well-known means of applying a solution of a treating agent to a substrate can be used such as spraying. Before application to the fabric the pH of the solution should be adjusted to less than 7, preferably 3 to 5, by the addition of an acid.

After the solution containing the coupling agent has been applied to the fibrous glass substrate, the substrate is dried by heating, preferably at a temperature of at least 80° C. During this drying procedure reaction takes place between the coupling agent and the surface of the glass. The fibrous glass substrate with the above coupling agent applied thereon can be stored for a substantial period of time before being impregnated with a thermosetting resin. Particularly good shelf life is obtained with the coupling agents illustrated by equation I, wherein both hydrogens of a primary amine starting material are replaced. When the fibrous glass substrate, e.g., glass fabric, and the final laminated product are made by different manufacturers, the coupling agent can be applied by the manufacturer of the fibrous glass substrate.

The coupling agents of this invention form strong, durable water resistant bonds between fibrous glass and thermosetting resins such as epoxy resins, polyester resins (particularly the unsaturated alkyd-styrene type) and melamine resins. Laminated materials, which retain their strength properties (particularly their flexural strength) after prolonged exposure to water, can be obtained by superimposing layers of fibrous glass material treated with a coupling agent of the present invention, impregnating the assembly with a thermosetting resin and a hardener or catalyst and then subjecting the assembly to heat and pressure.

The following examples are given to further illustrate the present invention.

EXAMPLE 1

To 1500 g. (6.8 moles) of gamma-aminopropyltriethoxy silane, $(C_2H_5O)_3Si(CH_2)_3NH_2$, placed in a three-neck flask equipped with stirrer, thermometer, reflux condenser and addition funnel, 1260 g. (13.6 moles) of epichlorohydrin were added over a 2-hour period with stirring while cooling in ice water. After the addition of the epichlorohydrin was completed, stirring and cooling were continued for an additional 4-hour period, after which time the exothermicity ceased. During the addition and the subsequent 4-hour period the temperature was maintained between 25°-35° C. The product obtained was slightly viscous and light amber in color.

The reaction product was determined to be the silyl amine compound of the formula

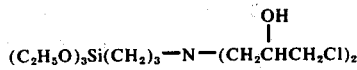

$$(C_2H_5O)_3Si(CH_2)_3-\underset{}{N}-(CH_2\overset{OH}{C}HCH_2Cl)_2$$

This product was diluted with methanol to give a solution containing 50 percent by weight of the product.

EXAMPLE 2

Example 1 was repeated but the reaction was carried out is methyl cellosolve medium. The amount of methyl cellosolve used was 23 percent based on weight of the total reactants.

The epichlorohydrin was added to the methyl cellosolve solution of the gamma-aminopropyltriethoxy silane in nitrogen atmosphere over a period of two hours, maintaining the temperature between 70°-80° C. Upon completion of the addition, the reaction mixture was held at 80° C. for an additional hour and there was obtained the same silyl amine compound as in Example 1. After cooling, the reaction mixture was diluted with additional methyl cellosolve to obtain a product containing 50 percent by weight of the silyl amine compound.

EXAMPLE 3

Example 1 was repeated but for each mole of gammaaminopropyltriethoxy silane only one mole of epichlorohydrin was used. The main reaction product was

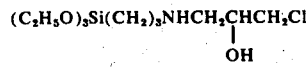

$$(C_2H_5O)_3Si(CH_2)_3NHCH_2\underset{OH}{C}HCH_2Cl$$

EXAMPLE 4

A glass fabric having a weight of 9 ounces per square yard and a thread count of 56 × 54 (warp × filling), was heat-cleaned at 355° ± 15° C. for 72 hours, then washed by a 0.1 percent aqueous solution of acetic acid, and finally rinsed by water and dried.

The products of Examples 1 and 3, and the commercially available coupling agents gamma-aminopropyltriethoxy silane (APS), gamma-epoxypropyltriethoxy silane (EPS) and gamma-chloropropyltriethoxy silane (CPS) were made into 1 percent by weight solutions in water (pH adjusted to 4.0 with acetic acid) and applied as a finish to samples of the glass fabric by a padding operation. In the padding operation, the cloth, impregnated with the solution, was squeezed as it passed between two pad rolls. The finish or coupling agent was dried on the fabric by heating at approximately 120° C. for two minutes. The amount of the finish on the glass fabric was of the order of 0.3 – 0.4 percent by weight of the fabric.

The glass fabric samples treated with the coupling agents were used to prepare epoxy resin-glass laminates.

The resin composition contained an epoxy prepolymer, Epon 828, a hardener and a curing agent. Epon 828 (sold by Shell Chemical Co.) is a thermosetting liquid which is predominantly 2,2-bis[p-(2,3 epoxypropyl)phenyl] propane (molecular weight: 340), along with some closely related, higher-molecular-weight compounds also derived from glycidyl ethers of p,p-isopropylidenediphenol, so the overall average molecular weight is approximately 380. Specifications call for one gram equivalent of epoxide per 188 ± 4 grams of resin, and a viscosity of 130 ± 30 poises at 25° C.

The hardener for the epoxy prepolymer was Nadic Methyl Anhydride which has the formula:

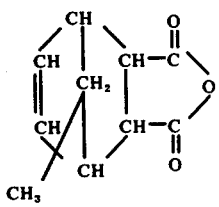

and the curing agent was N,N-dimethyl-benzylamine (BDMA). The Epon 828/NMA/BDMA weight ratio was 100/91/1. The Epon 828 prepolymer was heated to 80° C. and the NMA and BDMA were added to the hot prepolymer while stirring. The glass fabric was impregnated with the freshly prepared prepolymer-hardener — curing agent blend by a wet lay-up procedure wherein the plies of fabric were laid upon each other and wet with the liquid prepolymer.

To prepare for the wet lay-up, the glass fabrics having the coupling agents on them were cut into 12.5 by 16 inch rectangles. These pieces were stacked, six at a time, with yarns parallel on a bag that would subsequently seal in molten components during the pressing operation soon to follow. The bag was made of polyester film, specifically from ethylene glycol terephthalate polymer.

The lay-up was assembled on a plate heated to about 50° C. to make the prepolymer-hardener blend less viscous, thereby facilitating impregnation of the plies of fabric. A pool of freshly prepared prepolymer-hardener blend surrounded the stacked plies of glass fabric. Additional plies were added to give a total of 13 plies in each stack and more prepolymer-hardener blend was applied until all stacked plies were saturated. Just prior to sealing the bag holding the full stack of saturated plies, excess fluids (including entrapped air) was squeezed out by applying a rolling pin.

The impregnated bubble-free glass fabric was closed in the bag, which was then placed in a hot laminating press with 0.115 inch thick shims to maintain that thickness. The press, initially at 93° C. was held at that temperature for 30 minutes, then kept at 120° C. for 35 minutes and finally heated to 150° C. for 35 minutes to cure the thermosetting composition. Immediately thereafter, cool water was circulated through tubes in the top and bottom plates to cool them and the laminate in order to prevent hot warping. The laminate was then postcured for 24 hours at 177° C. in an oven.

Specimens of the laminates suitable for evaluation on an Instron strength testing machine were made by sawing them into 0.5 by 4-inch rectangles and machining them to dimensions necessary to subject them to the following tests:

| Flexural Strength | ASTM Test Method D 790-59T |
| Compressive Strength | ASTM Test Method D 695-61T |
| Tensile Strength | ASTM Test Method D 638-61T |

Specimens of each laminate were tested (a) directly as a set without having been exposed to the destructive action of water, (b) after immersion in boiling water for two hours, and (c) after immersion in boiling water for 72 hours. The immersion in boiling water for 72 hours is roughly equivalent to immersion in water at 20° C. for around three years with respect to its weakening effect on strength values of a laminate. The two-hour boil approximates the effects of a month in water at 20° C. Immersion in boiling water is used as an accelerated method for assessing the permanence of laminates as measured by strength properties. All specimens were wiped dry before strength properties were measured.

The physical properties of the laminates prepared are shown in Table I. All three of the above strength properties were determined for the samples (RT) which were not exposed to boiling water while flexural strength was determined for the samples exposed to boiling water.

TABLE I

| Coupling Agent | APS | EPS | CPS | Prod. of Ex. 1 | Prod. of Ex. 3 |
|---|---|---|---|---|---|
| Flex (PSI × 10³) | | | | | |
| RT | 74.9 | 90.6 97.5 | 102.9 | 102.3 | |
| 2 hour boil | 79.7 | 89.4 | 95.0 | 100.0 | 102.8 |
| 72 hour boil | 77.7 | 85.0 | 73.6 | 91.4 | 92.9 |
| Tensile (PSI × 10³) | 55.1 | 68.4 | 72.1 | 73.5 | 73.0 |
| Comp (PSI × 10³) | 63.6 | 67.6 | 62.5 | 70.0 | 67.2 |
| Percent Resin | 29.9 | 30.4 | 30.5 | 31.0 | 30.0 |
| Thickness | .114 | .115 | .115 | .115 | .115 |
| Spec. Gravity | 1.89 | 1.88 | 1.93 | 1.88 | 1.87 |

It will be apparent that many modifications and variations can be effected without departing from the scope of the novel concepts of the present invention and the illustrative details disclosed are not to be construed as imposing undo limitations on the invention.

We claim:

1. A compound of the formula

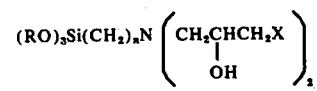

wherein
R is alkyl of 1 to 5 carbon atoms,
X is chlorine or bromine, and
n is an integer of 1 to 4.

2. A compound of the formula

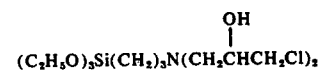

* * * * *

UNITED STATES PATENT AND TRADEMARK OFFICE
CERTIFICATE OF CORRECTION

PATENT NO. : 4,032,554
DATED : June 28, 1977
INVENTOR(S) : Richard G. Adams and Stephen B. Sello It is certified that error appears in the above-identified patent and that said Letters Patent are hereby corrected as shown below:

Column 1, line 25 should read $Z-N-CH_2-CH\overset{O}{\overbrace{\phantom{---}}}CH_2$ Column 6, TABLE I, line 33 should read

| Coupling Agent | APS | EPS | CPS | Prod. of Ex. 1 | Prod. of Ex. 3 |
|---|---|---|---|---|---|
| RT | 74.9 | 90.6 | 97.5 | 102.9 | 102.3 |

Signed and Sealed this

Twelfth Day of December 1978

[SEAL]

Attest:

RUTH C. MASON
Attesting Officer

DONALD W. BANNER
Commissioner of Patents and Trademarks